United States Patent [19]

Zerbes

[11] 4,139,555

[45] Feb. 13, 1979

[54] RECOVERY OF (1-S)-2-OXO-BORNANE-10-SULPHONATE

[75] Inventor: Rudolf Zerbes, Wuppertal, Fed. Rep. of Germany

[73] Assignee: Bayer Aktiengesellschaft, Leverkusen, Fed. Rep. of Germany

[21] Appl. No.: 795,845

[22] Filed: May 11, 1977

[30] Foreign Application Priority Data

May 8, 1976 [DE] Fed. Rep. of Germany ....... 2620369

[51] Int. Cl.$^2$ ............................................ C07C 143/20
[52] U.S. Cl. ................................ 260/503; 260/501.14; 260/564 A
[58] Field of Search ............................ 260/503, 501.14

[56] References Cited

U.S. PATENT DOCUMENTS

| | | | |
|---|---|---|---|
| 3,520,926 | 7/1970 | Bollag et al. | 260/503 |
| 3,816,531 | 6/1974 | Bruce et al. | 260/501.14 |
| 4,049,703 | 9/1977 | Buss | 260/503 |

Primary Examiner—Joseph E. Evans

Attorney, Agent, or Firm—Sprung, Felfe, Horn, Lynch & Kramer

[57] ABSTRACT

A process has been developed for the recovery of (1-S)-2-oxo-bornane sulphonic acid (D-camphor-β-sulphonic acid) from contaminated aqueous solutions, particularly from those which arise as mother liquors from the resolution of the racemates of amino compounds wherein said solutions are treated with guanidine bases (or soluble salts thereof) of the formula

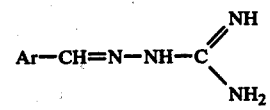

in which Ar is an optionally substituted aryl radical at pH about 3.5 to 7.5 and the guanidinium camphorsulphonate is separated off and split. The process is effective even where the mother liquors are contaminated with large amounts of inorganic salts.

12 Claims, No Drawings

RECOVERY OF (1-S)-2-OXO-BORNANE-10-SULPHONATE

BACKGROUND OF THE INVENTION

The subject of the invention is a process for the recovery of (1-S)-2-oxobornanesulphonic acid (D-camphor-β-sulphonic acid) from contaminated aqueous solutions.

(1-S)-2-Oxo-bornane-10-sulphonic acid, hereinafter referred to for brevity as camphorsulphonic acid (further abbreviated CSA) is an important auxiliary acid in the resolution of racemates of amino compounds.

It has long been known that, for example, racemic aminoacids form diastereomeric salts with an optically active acid, and these salts can in many cases be resolved by fractional crystallisation (H. Bayer, Lehrbuch d. org. Chemie (Textbook of Organic Chemistry), 8th edition, 1961, page 258). The corresponding optically active aminoacids can be obtained from the resolved diastereomeric salts by decomposing them into their components. This principle is also the basis of the optical resolution of DL-2-phenylglycine with (1-S)-2-oxobornane-10-sulphonic acid, referred to in the past as D-camphor-β-sulphonic acid, and hereinafter referred to for brevity as camphorsulphonic acid (further abbreviated CSA), which is described in Beilstein E III, 14, 1,187. (Timmermanns and Motiuk Bl. Soc. chem. Belg. 41 (1932), 402).

The preparation of an optical antipode by fractional crystallisation as a rule gives only moderate yields. In the process described for the preparation of D-2-phenylglycine, which is an important intermediate for the preparation of valuable penicillin and cephalosporin antibiotics, the yield achieved is also only from 30 to 35%, relative to the racemic aminoacids employed.

Using this process, equimolar amounts of DL-2-phenylglycine and CSA are dissolved in water at elevated temperatures and on cooling, the more sparingly soluble D-enantiomer crystallises out as the camphorsulphonate. From the mother liquor, the excess phenylglycine is recovered after alkaline racemisation and bringing the mixture to the isoelectric point, whilst the camphorsulphonic acid which is not co-precipitated and which is contaminated with large amounts of inorganic salts, is lost.

Even if, in a preferred procedure, ½ equivalent of the camphorsulphonic acid is replaced by hydrochloric acid, the loss of the valuable optically active acid remains considerable. In addition, the large amount of sodium chloride (potassium chloride) which, because of the nature of the process, passes into the waste liquors prevented the recovery of the CSA still present therein.

Such a process can only be carried out economically on an industrial scale if the valuable auxiliary materials of the process, which cannot be converted to the end product, are recovered.

The following procedures for the recovery of camphorsulphonic acid have already been described:

According to the process of U.S. Pat. No. 3,221,046
1. an aqueous CSA solution is treated, at pH 3 to 6, with a water-immiscible solvent which contains a secondary amine of the type of the "liquid amines mixture." In this treatment, the CSA is extracted into the organic phase and is reextracted therefrom into water at pH 9. By using a smaller volume of water than that of the starting solution, the CSA becomes concentrated. This process has the great disadvantage that it has only been described for CSA-containing solutions which are free from inorganic salts. The use of these "liquid amines mixture" with waste waters such as result from the particularly economically described diastereomer resolution process with subsequent alkaline racemisation, led to considerable difficulties as a result of stable emulsions which cannot be eliminated even by various modifications of the process.

2. It is also known that acids, especially camphorsulphonic acid, can be isolated by the use of ion exchangers (G. N. Kulikova and J. T. Strukow, Pharm. Chem. J. 6, (1963) 6, 391-2). This process again presupposes that the CSA- containing solution is substantially free from inorganic salts. For the case of the splitting process described above, in which the resulting waste waters contain the camphorsulphonic acid in a very dilute form, alongside a four-fold to five-fold amount of inorganic salts, regeneration of the camphorsulphonic acid with ion exchangers is not realisable.

Surprisingly, these disadvantages and limitations are overcome by the process according to the invention.

SUMMARY OF THE INVENTION

This new process for the recovery of (1-S)-2-oxo-bornane-10-sulphonate from solutions contaminated with water-soluble salts of alkali metal hydroxides and mineral acids, e.g., sodium chloride, especially from those which arise as mother liquors from the resolution of the racemates of amino compounds, especially of the racemates of D,L-amino acids and more especially of D,L-2-phenylglycine racemate, is characterized in that the solutions are treated with guanidine bases of the formula

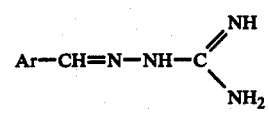

in which
Ar denotes an optionally substituted aryl radical, preferably a carbocyclic aryl radical, such as a phenyl or naphthyl radical and/or their water-soluble salts, at pH values of about 3.5-7.5, preferably at about pH 7, and the guanidinium camphorsulphonate formed is separated off and split.

Preferably, guanidine bases of the formula I, or their water-soluble salts,
in which
Ar represents a radical

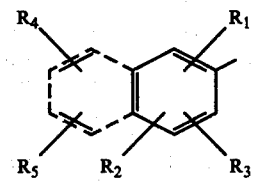

wherein
the broken lines are intended to indicate the possible presence of a naphthyl radical, and
$R_1$, $R_2$, $R_3$, $R_4$ and $R_5$, independently of one another, denote hydrogen, trifluoromethyl $C_1$–$C_4$ alkyl, aryl, $C_1$–$C_4$ alkoxy and aryloxy are used. Alkyl and alkoxy substituents preferably contain 1 to 2 carbon atoms. Aryl and aryloxy substituents are preferably phenyl, naphthyl, phenyloxy and naphthyloxy; said aryl and aryloxy substituents can be substituted, e.g., by chlorine or methoxy.

Benzalaminoguanidine bases of the formula I in which

Ar represents a radical

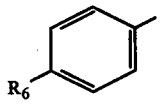

wherein $R_6$ denotes hydrogen, chlorine or methoxy and/or their water-soluble salts are particularly preferred.

In the process according to the invention for precipitating CSA from dilute aqueous solutions, the benzalaminoguanidine bases, in the form of their soluble salts, such as salts of strong acids, e.g., mineral acids or their soluble salts of carboxylic acids, such as $C_1$-$C_3$ alkane carboxylic acids, preferably their acetates, are added in the solid form, or, optionally, in the form of their components or as an aqueous solution, to the reaction mixture.

The bases of their salts are added in equimolar amounts to the CSA solution, if appropriate in an excess of up to about 20% in order to increase the yield.

The precipitation is carried out in the pH range of about 3.5 to about 7.5, preferably at a pH of about 7, in the preferred temperature range of about −5° to about 45° C.; a reaction temperature of about 25°–35° C. is particularly advantageous. The reaction times are between about 1 and about 12 hours, preferably between about 8 and about 10 hours.

CSA, which is in most cases present in the solutions in the form of its neutral salts, forms sparingly water-soluble salts with the bases employable according to the invention, the precipitation of which salts is not interfered with by the presence of even substantial amounts of foreign salts, for example sodium chloride. The precipitated guanidinium camphorsulphonate is separated off and split with strong bases, such as alkali metal bases preferably sodium hydroxide solution and potassium hydroxide solution, at temperatures of about −10° to about +30° C., preferably about 0° C., into, for example, sodium camphorsulphonate and guanidine base, which can be recycled, in this form, to the resolution process.

The application of the process according to the invention to the resolution of the racemate of D- and L-phenylglycine can be represented by the following scheme:

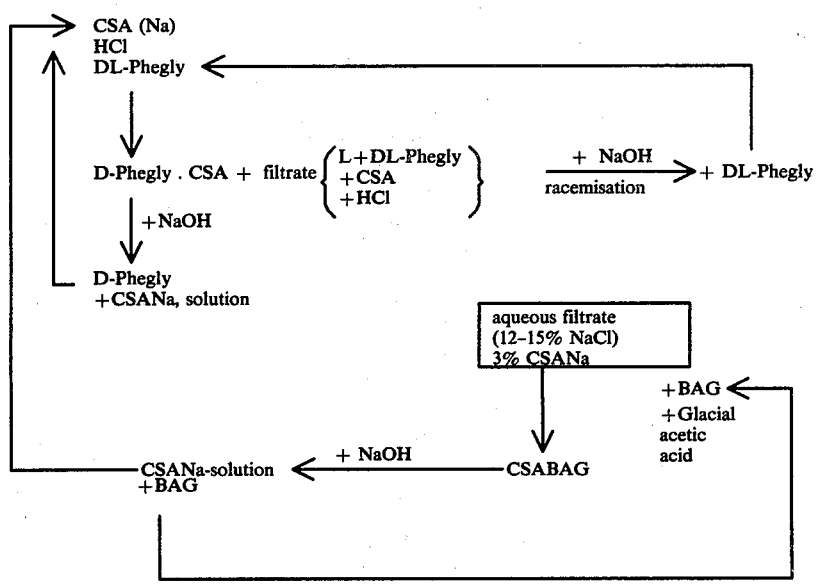

DL-2-Phenylglycine (DL-Phegly) is reacted with CSA, in the presence of hydrochloric acid, to give D-2-phenylglycine camphorsulphonate (D.Phegly.CSA) which is filtered off. The filtrate contains, in solution, excess CSA, L- and DL-2-phenylglycine and hydrochloric acid. The aminoacid is racemized with sodium hydroxide solution and precipitated out at the isoelectric point, and CSA is precipitated from the mother liquor by means of benzalaminoguanidine (BAG) as benzalaminoguanidiniumsulphonate (CSA-BAG). The sparingly soluble salt is separated off and split by means of sodium hydroxide solution to give the base and sodium camphorsulphonate, which can be reused for resolving the antipodes. D-2-Phenylglycine camphorsulphonate, on treatment with sodium hydroxide solution, gives D-2-phenylglycine and sodium camphorsulphonate, which can also be reused for splitting the antipodes.

The guanidine bases are prepared in accordance with methods known from the literature (Ann. 270, 35 (1892)). A particularly well-proven process for the preparation of benzalaminoguanidine acetate is reproduced in the experimental section which follows.

The process according to the invention is not only applicable to the mother liquors which arise in the course of the resolution of DL-2-phenylglycine, but can also be used for the recovery of camphorsulphonate, which arises in the resolution of the racemates of optically active amines or substituted 2-phenylglycines, such as are described in U.S. Pat. No. 3,221,046.

The examples which follow illustrate, but are not limitative of the invention.

Preparation of Benzalaminoguanidine 160 g aminoguanidine bicarbonate are suspended in 1.1 l water and brought into solution by means of 93-100 ml concentrated hydrochloric acid. 124.5 g benzaldehyde added at room temperature and 340 g of 50% strength potassium hydroxide solution are then allowed to run in. In the course thereof, the temperature rises to about 35°. Stirring is continued for a further hour, the mixture is cooled to 5° C. and the precipitate is filtered off and rinsed with 0.5 l water.

Yield: 185 g (97% of theory) Melting point: 180°–182°

Preparation of Benzalaminoguanidine Acetate

To prepare benzalaminoguanidinium acetate, 140 g benzalaminoguanidine are dissolved in 1.75 l ethyl acetate at 40°. At this temperature, 51.7 g glacial acetic acid are added dropwise and the mixture is then cooled to 5°–10° C. The benzalaminoguanidinium acetate is filtered off, washed with 150 ml ethyl acetate and dried at 50°.

Yield: 184 g (96% of theory) Melting point: 205°–207°.

EXAMPLE 1

(a) 361 g (1.42 M) sodium camphorsulphonate are dissolved in 1 l water, 357 ml (4.26 M) concentrated hydrochloric acid and 429 g (2.83M) DL-2-phenylglycine are added and the mixture is made up with water to 2,100 ml.

The solution is heated to 90°–95°, insoluble by-products are filtered off and the filtrate is slowly cooled to room temperature. It is seeded with 1 g D-2-phenylglycine camphorsulphonate at 75° C. The precipitate is filtered off and rinsed with 125 ml water.

The moist D-2-phenylglycine camphorsulphonate is suspended in 550 ml water, the suspension is heated to 70° and 85 g 45% strength sodium hydroxide solution are added. The temperature rises to 90°–95°.

The mixture is neutralized to pH 6.5–7 in 1 hour by means of about 14 ml 45% strength sodium hydroxide solution and the batch is kept at 85°–95° C. for 15 minutes and slowly cooled to 20°–25°. After filtering off, the precipitate is washed with 3 × 30 ml water and dried in vacuo at 70°–80°. Yield: 152 g (1.01 M) of D-2-phenylglycine $\triangleq$ 35% of theory (relative to DL-2-phenylglycine employed).

The filtrate obtained after the precipitation of the D-2-phenylglycine camphorsulphonate contains about 275 g L- and DL-2-phenylglycine and 95g camphorsulphonic acid, as well as hydrochloric acid and sodium chloride. It is rendered strongly alkaline (pH 12) with sodium hydroxide solution and heated for 2 hours to 95°. After cooling, and neutralizing, the racemic DL-phenylglycine is filtered off. The mother liquor contains about 2.85% camphorsulphonic acid (as the Na salt) and 12–15% sodium chloride, as well as small amounts of phenylglycine and further by-products, and is reacted with benzalaminoguanidine acetate in order to recover CSA.

(b) Precipitation of benzalaminoguanidinium camphorsulphonate (abbreviated CSABAG). 150 g (0.675 M) benzalaminoguanidinium acetate are added, at 20° C., to 5,000 ml of the mother liquor which contains 2.85% = 156 g (0.614 M) of sodium camphorsulphonate and ≈ 12% = 600 g of sodium chloride as well as small amounts of phenylglycine and other by-products. The mixture is stirred for 12 hours at 30° C. and the CSABAG which has precipitated is filtered off and rinsed with 300 ml water. The salt can be employed moist for splitting into sodium camphorsulphonate and benzalaminoguanidine.

Yield: 210 g (0.533 M) of CSABAG ( $\triangleq$ 87% of theory) Melting point: 205°–207°.

(c) Splitting of benzalaminoguanidinium camphorsulphonate with sodium hydroxide solution 362 g (0.92 M) CSABAG are suspended in 1,100 ml water. 82.5 g of 45% strength (0.93 M) sodium hydroxide solution are allowed to run in over the course of 30 minutes. The suspension is cooled to 0° and stirred for a further 30 minutes, and the precipitate is filtered off and rinsed with 300 ml water. Yield: 130 g (0.8 M) benzalaminoguanidine ( $\triangleq$ 87% of theory).

The filtrate about 1,600 ml, contains ≈ 11.5% of camphorsulphonic acid $\triangleq$ 209 g (0.9 M) as the sodium salt and can be employed for splitting the racemate of DL-2-phenylglycine.

EXAMPLE 2

Analogously to Example 1b, 33.8 g (0.134 M) of p-chloro-benzalaminoguanidinium acetate are stirred thoroughly with 1 l of the mother liquor for 2 hours at room temperature, the solution is cooled to 0° and the precipitate is filtered off and dried.

Yield: 52 g (0.121 M) $\triangleq$ 90.5% of theory, p-chloro-CSABAG Melting point: >220° C., with decomposition.

EXAMPLE 3

Analogously to Example 1 b and 2, 34 g (0.134 M) p-methoxy-benzalaminoguanidinium acetate are stirred with 1 l of the mother liquor for 6 hours, the mixture is cooled to 0° and the precipitate is filtered off and dried.

Yield: 54 g (0.127 M) $\triangleq$ 95% of theory p-methoxy-CSABAG Melting point: 203°–205° C.

EXAMPLE 4

110 g (0.68 M) benzalaminoguanidine are suspended in 800 ml water and brought into solution with 40.7 g (0.68 M) glacial acetic acid. This solution is allowed to run into 5 l of the mother liquor, the mixture is stirred for a further 6 hours at room temperature and the resulting precipitate is filtered off.

Yield: 227 g (0.576 M) $\triangleq$ 85% of theory of CSABAG Melting point: 205°–207° C.

What is claimed is:

1. A process for the recovery of (1-S)-2-oxo-bornane-10-sulphonate from contaminated aqueous solutions comprising treating the solution with a guanidine base, in solid form or in the form of an aqueous solution, said base having the formula

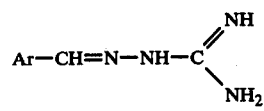   I in which
Ar denotes an unsubstituted or substituted aryl radical, or a water-soluble salt thereof, at a pH value of from about 3.5 to 7.5, and separating off and splitting the resulting guanidinium camphorsulphonate formed.

2. A process according to claim 1 wherein the contaminated solution is treated with a guanidine base of the formula I, in which Ar represents a radical

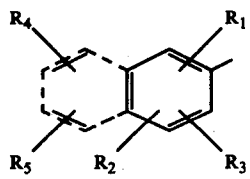

wherein

R$_1$, R$_2$, R$_3$, R$_4$ and R$_5$ independently of one another denote hydrogen, halogen, alkyl, aryl, alkoxy or aryloxy, or a water-soluble salt thereof.

3. A process according to claim 1 wherein the contaminated solution is treated with a guanidine base of the formula I in which Ar represents a radical

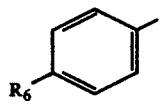

wherein

R$_6$ denotes hydrogen, chlorine or methoxy or a water-soluble salt thereof.

4. A process according to claim 1 wherein the contaminated solution is treated with an acetate of the said guanidine base.

5. A process according to claim 1 wherein the treatment is carried out at a pH of about 7.

6. A process according to claim 1 wherein the contaminated solution is treated at a temperature of from $-5°$ to $+45°$ C.

7. A process according to claim 1 wherein the contaminated solution is treated at a temperature of from $+25°$ to $+35°$ C.

8. A process according to claim 1 wherein the guanidinium camphorsulphonate is split by treatment with a strong base.

9. A process according to claim 8 wherein the strong base comprises sodium hydroxide solution or potassium hydroxide solution.

10. A process according to claim 1 wherein the splitting is carried out at a temperature in the range of from $-10°$ C. to $+30°$ C.

11. A process according to claim 10 wherein the splitting is carried out at a temperature of about $0°$ C.

12. A process according to claim 1 wherein the contaminated aqueous solution is obtained from the resolution of racemates of amino compounds.

* * * * *